(12) United States Patent
Pedro et al.

(10) Patent No.: US 8,440,144 B2
(45) Date of Patent: May 14, 2013

(54) METALLIC PHOTOCATALYTIC OXIDATION REFLECTOR COATED WITH TITANIUM DIOXIDE

(76) Inventors: Helder Pedro, Laval (CA); Ken Henricksen, Montreal (CA)

( * ) Notice: Subject to any disclaimer, the term of this patent is extended or adjusted under 35 U.S.C. 154(b) by 0 days.

(21) Appl. No.: 13/163,483

(22) Filed: Jun. 17, 2011

(65) Prior Publication Data

US 2012/0114532 A1 May 10, 2012

Related U.S. Application Data

(60) Provisional application No. 61/355,735, filed on Jun. 17, 2010.

(51) Int. Cl.
*B01J 19/08* (2006.01)

(52) U.S. Cl.
USPC ........ 422/186.3; 502/349; 502/350; 423/608; 423/610; 422/186

(58) Field of Classification Search ............... 422/186.3, 422/186; 423/608, 610; 502/349, 350
See application file for complete search history.

(56) References Cited

U.S. PATENT DOCUMENTS

| | | | |
|---|---|---|---|
| 2,446,461 | A | 8/1948 | Diver |
| 4,514,793 | A | 4/1985 | Andreasen |
| 4,961,127 | A | 10/1990 | Shemitz et al. |
| 5,369,558 | A | 11/1994 | Munz |
| 5,408,395 | A * | 4/1995 | Schmid et al. ................ 362/240 |
| 6,923,555 | B2 | 8/2005 | Byggmastar |
| 2005/0073843 | A1 * | 4/2005 | Berger et al. ................ 362/277 |

* cited by examiner

*Primary Examiner* — Xiuyu Tai
(74) *Attorney, Agent, or Firm* — Kelley Drye & Warren LLP

(57) ABSTRACT

Through innovative design of a titanium dioxide coated metal reflector, which uses the negative space of a U-shaped ultraviolet lamp, maximum airborne chemical, vapor and/or odor abatement through photochemical reaction, yet eliminates most UV irradiation obstruction emanating from the lamp, thereby insuring maximum germicidal effect.

2 Claims, 3 Drawing Sheets

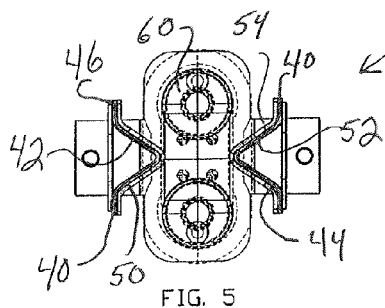
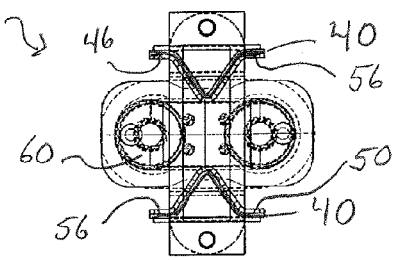
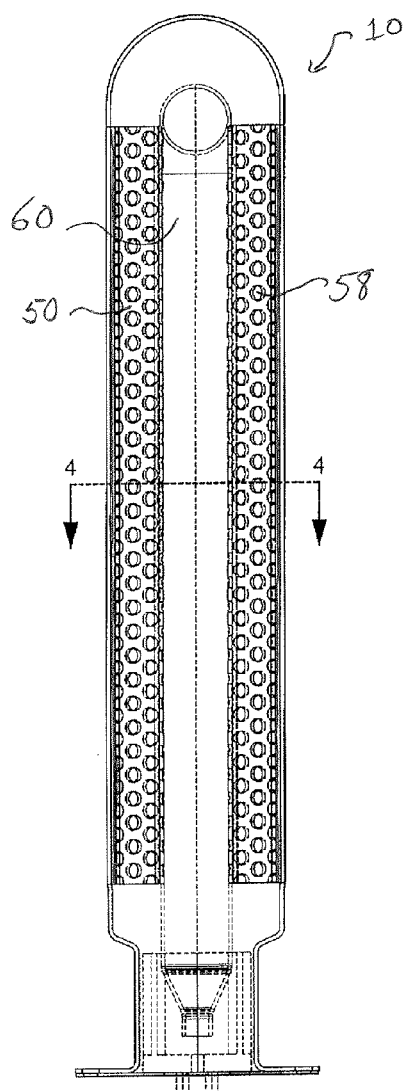
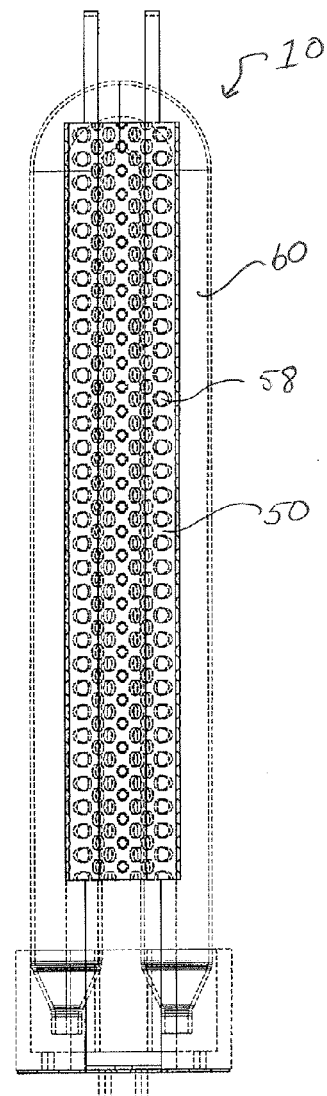

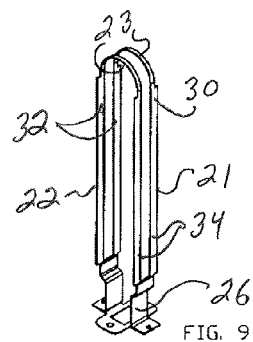
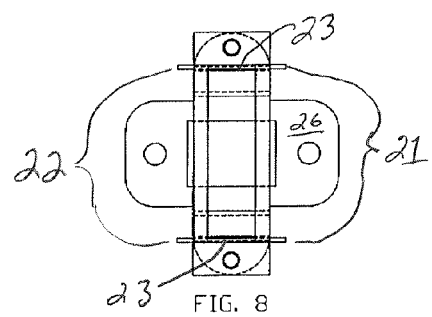
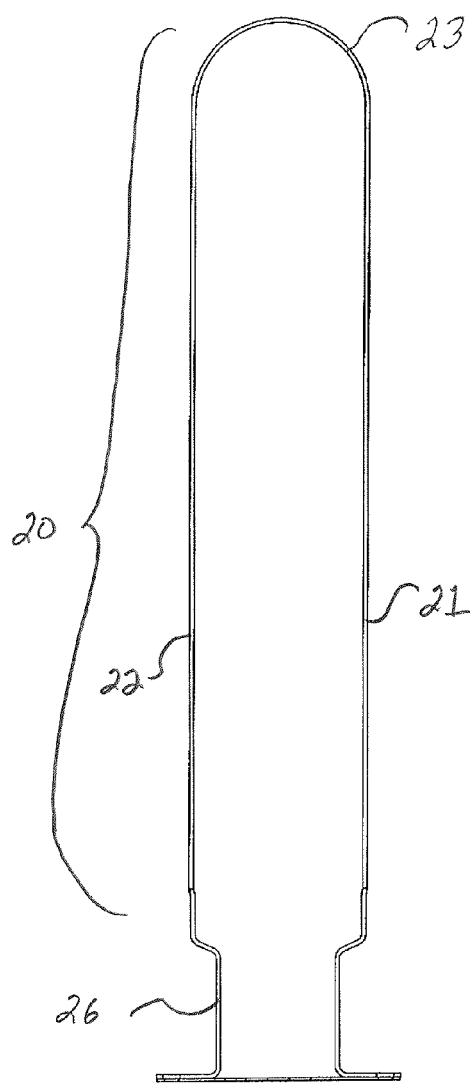
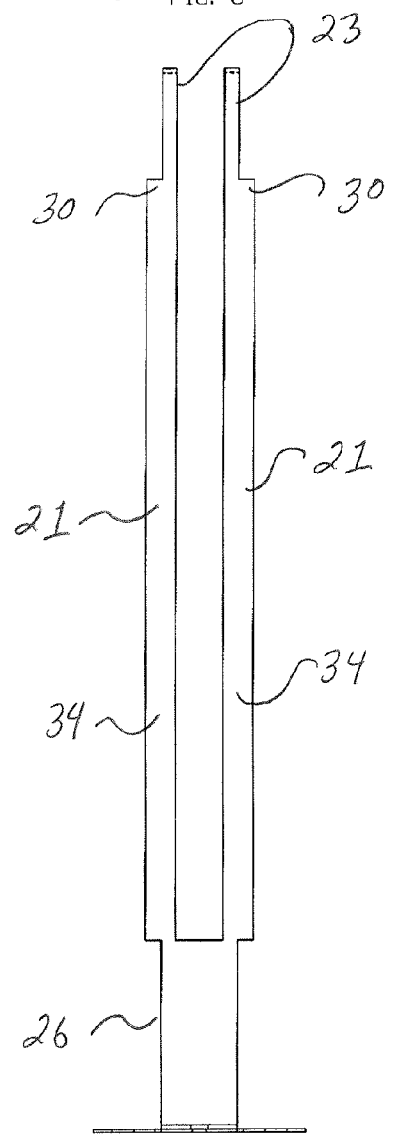
FIG. 9
FIG. 8
FIG. 6
FIG. 7

METALLIC PHOTOCATALYTIC OXIDATION REFLECTOR COATED WITH TITANIUM DIOXIDE

CROSS REFERENCE TO RELATED APPLICATIONS

This application claims priority to U.S. Patent Application No. 61/355,735, filed Jun. 17, 2010, which is herein incorporated by reference in its entirety.

FIELD OF THE INVENTION

The present invention relates to metallic photocatalytic oxidation reflector coated with titanium dioxide. More particularly, embodiments of the present invention relate to a metallic photocatalytic oxidation reflector coated with titanium dioxide to be used in conjunction with a UV lamp.

BACKGROUND OF THE INVENTION

Indoor pollution sources that release gases or particles into the air are the primary cause of indoor air quality problems. Inadequate ventilation can increase indoor pollutant levels by not bringing in enough outdoor air to dilute emissions from indoor sources and by not carrying indoor air pollutants out of the home.

As many as 8 out of 10 allergy sufferers have allergy symptoms year-round due to indoor air particles. Perennial allergy symptoms can be controlled by improving indoor air quality with air cleaners.

Unlike other types of air purifiers, UV air purifiers are designed to purify the air using ultraviolet ("UV") light. Various air pollutants including airborne viruses, mold, bacteria, yeast, and fungus are susceptible to UV radiation.

A photocatalytic UV air purifier uses broad spectrum UV light, which reacts with a thin-film titanium dioxide-based chemical catalyst, in the presence of water, to create hydroxyl radicals and super-oxide ions which oxidize volatile organic compounds (VOCs), and eliminate microorganisms adsorbed on the catalyst surface.

The photocatalytic air purifier is based on photocatalytic oxidation (PCO), an emerging air purifier technology that converts fine particles and toxic gasses into safer compounds.

Systems known in the art include either an open structure coated with titanium dioxide disposed in the same enclosure with a UV lamp, wherein the contaminated air passes through the open structure while irradiated with the UV light, or a system wherein a titanium dioxide coated substrate is placed at some distance from the UV lamp, and reflectors are placed at the side of the lamp not facing the substrate in order to reflect additional UV light toward the substrate.

At present, UV air purification systems rely on the intensity of the UV light available. What is needed in the industry is a reflector designed to increase the intensity or "killing power" of the UV lamp.

What is needed in the industry is a UV air purification system that can sterilize bacteria, viruses and mold spores. What is needed in the industry is a UV air purification system that can increase the range of dangerous airborne chemicals that can be neutralized safely and effectively. What is needed in the industry is a UV air purification system that can reduce airborne chemicals to smaller safer compounds, until only carbon dioxide and water vapor are left. What is needed in the industry is a UV air purification system that can remove substantially 100% of formaldehyde leaving only carbon dioxide and water vapor.

What is needed in the industry is a UV air purification system that is effective for: formaldehyde, radon, ammonia, mercury vapor, benzene, aldehydes, pesticides, butanol, carbon monoxide, exhaust fumes, molds, mycotoxins, PCBs, trichlorophenol, sulfur oxides, toluene, nitrous oxide, chloroform, dioxane, chlorotoluene.

What is needed in the industry is a UV air purification system that enables diffusion of the germicidal dosage from the UV lamp is enhanced in the confined chamber.

What is needed in the industry is a UV air purification system that provides photocatalytic oxidation for volatile organic compound ("VOC")s, chemicals and odors; and ultraviolet (UV) sterilization for microorganisms. What is needed in the industry is a system that combines the elements of the coated substrate and reflector within a certain proximity of the UV light source so as to increase efficiency of the UV irradiation, the surface area of the titanium dioxide coated substrate, and to occupy less overall space that known systems.

SUMMARY OF THE INVENTION

An advantage of embodiments of the Titanium Dioxide Photo-Catalytic Reflector according to an embodiment of the present invention remove substantially 100% of formaldehyde leaving only carbon dioxide and water vapor.

An advantage of embodiments of the present invention provide a UV lamp and reflector that sterilize bacteria, viruses and mold spores by destroying the DNA of the micro-organisms.

An advantage of embodiments of the present invention provide a Titanium Dioxide Photo-Catalytic Reflector dramatically increases the range of dangerous airborne chemicals that can be neutralized safely and effectively.

An advantage of embodiments of the present invention provide a titanium dioxide (TiO2) coating in conjunction with the UV light, creating an oxidizing process that instantly breaks molecular bonds and reduces airborne chemicals to smaller safer compounds, until only carbon dioxide and water vapor are left.

An advantage of embodiments of the present invention are for substantially eliminating: formaldehyde, radon, ammonia, mercury vapor, benzene, aldehydes, pesticides, butanol, carbon monoxide, exhaust fumes, molds, mycotoxins, PCBs, trichlorophenol, sulfur oxides, toluene, nitrous oxide, chloroform, dioxane, chlorotoluene.

An advantage of embodiments of the present invention is enabling diffusion of the germicidal dosage from the UV lamp to enhance its effectiveness.

An advantage of embodiments of the present invention is providing photocatalytic oxidation for volatile organic compound ("VOC")s, chemicals and odors; and ultraviolet (UV) sterilization for microorganisms.

An advantage of embodiments of the present invention is a system that combines the elements of the coated substrate and reflector disposed within a certain proximity of the UV light source so as to increase efficiency of the UV irradiation and the surface area of the titanium dioxide coated substrate, and to occupy less overall space that known systems.

In accordance with embodiments of the present invention, the present invention is a metallic photocatalytic oxidation system comprising: two elongated U support structures having two first arm portions each having a first and second end; two second arm portions each having a first and second end; and two U shaped connector bridges; and a base; wherein a first end of one of the first arm portions is connected to one end of one of the U shaped bridges; wherein the first end of one of the second arm portions is connected to the other end of the same U shaped bridge; wherein the second U shaped bridge connects the first ends of the other first arm portions and second arm portions in a corresponding manner; wherein the second ends of both the first arm portions and the second arm portions are connected to the base such that both elongated U structures are in a fixed position parallel to one another forming two elongated U structures facing one another in a mirror image position. The metallic photocatalytic oxidation system also comprises a flange disposed on each of first arm portions and second arm portions; wherein the flange extends outwardly towards an exterior of the support structures such that a first flat surface of the flange extending from the first arm portion opposes and is parallel to a first flat surface extending outwardly from the second arm portion that is connected to the same U shaped bridge; wherein a second pair of flanges are arranged correspondingly on the second pair of the first arm portions and the second arm portions; wherein the flange extends from the second end of the first and second arm portions to near the first end of the first and second arm portions. The metallic photocatalytic oxidation system may further comprise: a UV irradiation source; an elongated substrate layer having a first surface and a second surface; wherein the elongated substrate is V shaped in cross section along its length having a substrate layer flange running along the length of the longitudinal edges of the substrate layer; wherein the first surface forms an interior portion of the V shape and substrate layer flange and the second surface forms an exterior portion of the V shape and substrate layer flange; wherein the substrate layer is dimensioned such that the first surface of the substrate layer flange aligns and attaches to the first side of the support structure flange disposed on the first and the second arm portions of the support structure; wherein one first substrate layer is attached to the structure flange joining the two first arm portions; wherein an apex of the V shaped substrate layer faces the second arm portions; and wherein the first surface of the substrate layer flange a second substrate layer is attached to the first side of the structure flange disposed on second arm portions such that the apex of the V shape of the second of two substrate layers faces the apex of the V shaped structure of the first of two substrate layers. The metallic photocatalytic oxidation system may further comprise: a coated substrate layer of the same general dimensions and shape as substrate layer; the coated layer having a first surface, a second surface, and a flange; wherein the first surface forming the interior portion of the V shape and the second surface forming the exterior portion of the V shape, and each of two coated substrate flanges are attached to longitudinal edges of the coated substrate; wherein the coated substrate is sized to fit over the second surface of the substrate layer; wherein the first surface of the coated substrate layer flange is in contact with the second surface of substrate layer flange; the coated substrate layer having a plurality of openings over at least a portion of the coated substrate layer.

These and other embodiments of the present invention are more fully described in connection with the detailed description.

BRIEF DESCRIPTION OF THE DRAWINGS

The accompanying drawings, which are incorporated in and constitute a part of this specification, illustrate embodiments of the invention and with the description, serve to explain the principles of the invention. Where appropriate, the same reference numerals refer to the same or similar elements.

FIG. 2 is a side elevation view of a UV reflector according to an embodiment of the present invention.

FIG. 3 is a front elevation view of a UV reflector according to an embodiment of the present invention.

FIG. 4 is a cross sectional view taken along line 4-4 in FIG. 2 of a UV reflector according to an embodiment of the present invention.

FIG. 5 is a top plan view of a UV reflector according to an embodiment of the present invention.

FIG. 6 is a side elevation view with the internal feature removed of a UV reflector according to an embodiment of the present invention.

FIG. 7 is a front elevation view of a UV reflector according to an embodiment of the present invention.

FIG. 8 is a top plan view of a UV reflector according to an embodiment of the present invention.

FIG. 9 is a perspective view of a UV reflector according to an embodiment of the present invention.

DETAILED DESCRIPTION OF EMBODIMENTS OF THE INVENTION

Figure 1:
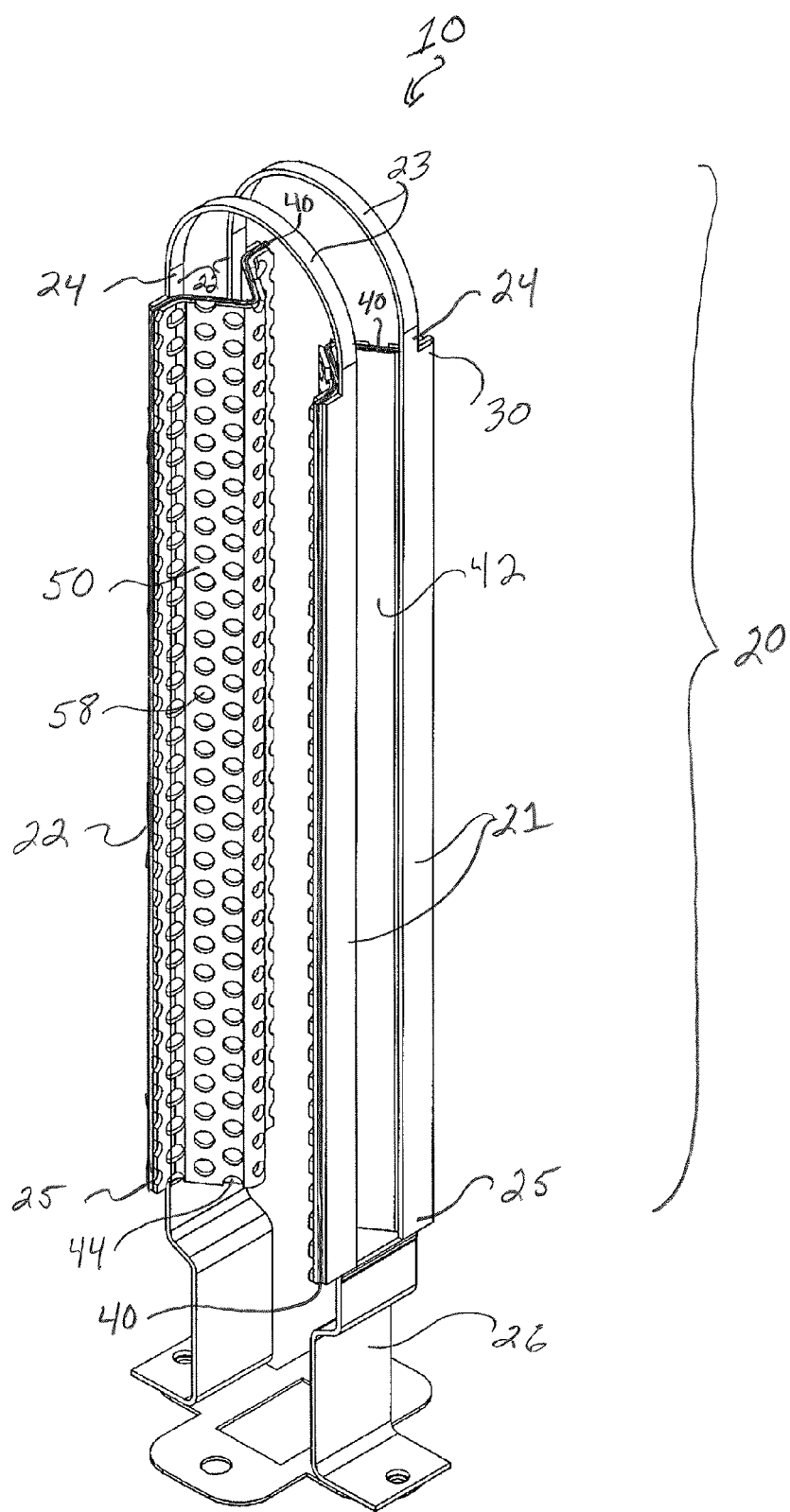
FIG. 1 is a perspective view of a UV reflector according to an embodiment of the present invention.

Reference now will be made in detail to the apparatus and methods consistent with implementations of the present invention, examples of which are illustrated in the accompanying drawings. The appended claims define the scope of the invention, and the following description does not limit that scope.

One embodiment of the present invention is a UV air purification system that provides photocatalytic oxidation for volatile organic compound ("VOC")s, chemicals and odors; and ultraviolet (UV) sterilization for microorganisms.

Applicant's technology, a process whereby chemical contaminants including many harmful VOCs, as well as many contaminants that cause strong odors, are destroyed using a process known as photocatalytic oxidation ("PCO"). This technology significantly increases the range of dangerous airborne chemicals that can be neutralized safely and effectively by the system.

Titanium Dioxide Photocatalytic Oxidization is used in laboratories for both air and water purification, the Photocatalytic Oxidation ("PCO") process is as follows. A metal surface coated with a metal oxide is irradiated with UV light to produce hydroxyl radicals and super-oxide ions. The hydroxyl radicals and super-oxide ions break the molecular bonds of chemicals they come into contact with and degrade them into smaller compounds, that are further broken down until only carbon dioxide and water vapor are left. For maximum efficiency, the process requires a sufficient surface area of reflective metal coated with a metal oxide to be positioned at a critical distance from the UV lamp while still allowing a good flow of air to bring the airborne chemicals into contact with the resulting hydroxyl radicals and super-oxide ions.

Known systems use planar filter structures coated with titanium dioxide, and some systems employ reflectors placed behind the UV light source to direct additional reflected light from behind the light source onto the planar filter. An embodiment of the present invention combines the reflector and titanium coated substrate into one structure, thereby increasing the efficiency of the system, while having a smaller footprint than is necessary for the other known systems.

Through innovative design of a titanium dioxide coated metal reflector, which uses the negative space of a U-shaped ultraviolet lamp, maximum airborne chemical, vapor and/or odor abatement through photochemical reaction, yet eliminates most UV irradiation obstruction emanating from the lamp, thereby insuring maximum germicidal effect.

A reflective surface coated with Titanium dioxide (TiO2) is irradiated with UV light to produce hydroxyl radicals and super-oxide ions. Through oxidation, the hydroxyl radicals and super-oxide ions break the molecular bonds of chemicals (VOCs) that they come into contact with and break them into smaller, safer compounds. These compounds are further broken down until only harmless carbon dioxide and water vapor remain.

In addition to activated the oxidation process of Applicant's technology, the ultraviolet lamp produces UV-C light of much greater intensity than sunlight. The intense UV light penetrates the cell wall of the microorganism and destroys its DNA thereby rendering it incapable of causing illness. UV sterilization has many advantages over conventional methods of killing microbiological contaminants in that it is extremely effective, chemical free, produces no harmful bi-products, produces limited excess heat, is energy-efficient, is very easy to maintain, and is cost effective to both purchase and maintain. The "U" shaped UV lamp in embodiments of Applicant's present invention is roughly double the length of competitor's lamps, allowing for a much higher UV dose.

An embodiment of the present invention provides broad spectrum contaminant removal capacity and enhanced removal of airborne chemicals and VOCs.

Applicant's titanium dioxide ($TiO_2$) coating in conjunction with the UV light, creates an oxidizing process that instantly breaks molecular bonds and reduces airborne chemicals to smaller safer compounds, until only carbon dioxide and water vapor are left.

Applicant's $TiO_2$ coated reflector according to an embodiment of the present invention provides a large amount of $TiO_2$ coated surface area (115% of the width of the UV lamp.) The UV lamp may be a 20 watt UV Germicidal Lamp. The angled reflector design maximizes the range of photo-catalytic oxidation within a filter chamber and increases the germicidal effect of the lamp. The UV germicidal lamp maintains 98% of its direct irradiation intensity due to the interior position of the $TiO_2$ coated reflector. Particulate pollution may be stopped by a HEPA filter before reaching the reflector to assist in keeping the coated surface cleaner and more effective.

As shown in FIG. 1, $TiO_2$ coated reflector assembly 10 is comprised of two generally elongated U support structures 20 comprising two first arm portions 21 having a first 24 and second 25 end, two second arm portions 22 having a first 24 and second 25 end, and two generally U shaped connector bridges 23. First end 24 of one of first arm portions 21 is connected to one end of one of U shaped bridges 23. The first end of one of second arm portions 22 is connected to the other end of the same U shaped bridge 23. The second U shaped bridge 23 connects first ends 24 of the other first arm portions 21 and second arm portions 22 in the same manner. Second ends 25 of both first arm portions 21 and second arm portions 22 are connected to base 26 such that both elongated U structures 20 are in a fixed position parallel to one another forming two elongated U structures 20 facing one another in a mirror image position.

As shown in FIGS. 7 and 9, Flange 30 is disposed on each of first arm portions 21 and second arm portions 22. Flange 30 extends outwardly towards the exterior of structure 20 such that a first flat surface 32 of flange 30 extending from a first arm portion 21 faces, opposes, and is parallel to, a first flat surface 32 extending outwardly from second arm portion 22 connected by the same U shaped bridge 23. A second pair of flanges 30 are arranged similarly on the second pair of first arm portions 21 and second arm portions 22. Flange 30 extends from second end 25 of first and second arm portions 21 and 22 disposed adjacent to base 26 to near first end 24 of first and second arm portions 21 and 22, respectively.

Referring back to FIGS. 1, and 2, 4, 5, elongated substrate layer 40 (filled line) having a first surface 42 and a second surface 44 is generally V shaped in cross section along its length and comprises a substrate layer flange 46 running along the length of the longitudinal edges of substrate layer 40. First surface 42 forms the interior portion of the V shape and first surface 42 of substrate layer flange 46 and second surface 44 forms the exterior portion of the V shape and second surface 44 substrate layer flange 46. Substrate layer 40 with flange 46 is dimensioned such that first surface 42 of substrate layer flange 46 is aligned with and may attach to first side 32 of support structure flange 30 disposed on first and second arm portions 21 and 22 of support structure 20. One first substrate layer 40 is attached to flange 30 joining two first arm portions 21, wherein the apex of the V shaped structure faces second arm portions 22. Substrate layer flange 46 first surface 42 of a second substrate layer 40 is attached to first side 32 of flange 30 disposed on each of second arm portions 22, such that the apex of the V shaped structure of second substrate layer 40 faces the apex of the V shaped structure of first substrate layer 40. Substrate layer 40 may be made of any suitable material, and may be reflective or non-reflective.

As shown in FIGS. 1-5, coated substrate layer 50 is of the same general shape, size, and dimension as substrate layer 40. Coated layer 50 comprises first surface 52, second surface 54 and flange 56. As with substrate layer 40, first surface 52 of coated substrate 50 forms the interior portion of the V shape and flange 56, second surface 54 forms the exterior portion of the V shape and flange 56, and each of two flanges 56 are attached to the longitudinal edges of coated substrate 50. Coated substrate 50 is dimensioned, shaped, and sized to fit over or on top of second surface 44 of substrate layer 40. First surface 52 of flange 56 of coated substrate 50 is in contact with second surface 44 of flange 46 of substrate layer 40. Other portions of first surface 52 of coated substrate 50 may be in contact with second surface 44 of substrate 40, but it is not necessary. Coated substrate 50 may have a plurality of openings 58 over all or a portion of its surface. Openings 58 may be circular or any other suitable shape and may form a honeycomb pattern, linear pattern, mesh pattern, or any other suitable pattern. Coated substrate 50 may be coated on second surface 54 to include the interior surfaces of openings 58. Coated substrate 50 may also be coated on first surface 52, to include the interior surfaces of openings 58, or both first and second surfaces 52 and 54, respectively. Coated substrate 50 may be comprised of any suitable material, including, but not limited to, aluminum, ceramic, paper, etc. Coated substrate 50 may be coated with any suitable metallic coating capable of PCO, including, but not limited to titanium dioxide.

As shown in FIGS. 2-5, assembly 10 comprises UV irradiation source 60. UV source 60 may comprise a U shaped UV bulb mounted in an appropriate housing such that the U shape of UV source 60 is mounted in a perpendicular orientation to the U shape of support structure 20. UV source 60 should be mounted such that the apex of the V shape of coated substrate 50 is in close proximity to the interior of the two arms of U shaped UV source 60.

FIG. 6 is a side elevation view of support structure 20 showing one pair of first and second arm portions 21 and 22, respectively, one U bridge connector 23, and base 26. FIG. 7 is a front elevation view of support structure 20 showing a pair of first arm portions 21, a pair of U bridge connectors 23, a pair of flanges 30, and base 26. In this view, second side 34 of first arm portions are visible.

FIG. 8 is a top plan view of support structure 20 showing first arm portions 21, second arm portions 22, U shaped connectors 23, and base 26. FIG. 9 is a perspective view of support structure 20 showing first arm portions 21, second arm portions 22, U shaped connector 23, first side 32 and second side 34 of flange 30, and base 26.

EXAMPLE

The Metallic Photocatalytic Reflector coated with Titanium Dioxide according to an embodiment of the present invention is shown in FIGS. 1-9.

FIG. 1 represents the Reflector from a side angle of about 30 degrees illustrating the shape of the reflector panels. The UV light cradles itself with one of its legs on either side of the V-shaped reflection surface. The lamp sits between both V-shaped reflectors, which continue below and around the UV lamp.

FIG. 3 illustrates the reflector if viewed straight ahead (or straight behind) 0 or 180 degrees. The width is 0.625", and the height is 8.821". The Reflector forms a U when viewed from the side, FIG. 2, and bottom view, FIGS. 4 and 5, we can see how the reflector is shaped, the circular elements represent the UV light in FIGS. 4 and 5, total depth of 1.4", a gap of 0.534" and 2 panels folded into opposing "V" shapes. Each V has a leg measuring 0.433".

FIGS. 2-5 illustrate the reflector as it would be viewed with the UV lamp sitting with the Reflector's bracketing.

The specially shaped metal reflector coated with Titanium dioxide (TiO2), provides 115% the surface of the ultraviolet lamp, deriving a greatly optimized photo-catalytic reaction and improved vapor chemical abatement and odor remediation capacity. By optimizing the UV lamp's power, strength and dimension to 115% of its normal output, the surface area, combined with the reflector's shape and focal distance with relation to the lamp, improves the performance without increasing electrical power consumption.

The design of the metal reflector is so innovative as it is 98% obstruction free with relation to the ultraviolet light's irradiation/illumination. This means that the UV lamp is virtually un-impeded with reference to its germicidal properties. Therefore nothing is compromised to derive the photocatalytic oxidation effect.

By its very nature the reflector enhances the Ultraviolet lamp's germicidal properties as it adds to the UV irradiation by the sum of its surface area, and also intensifies a portion of the UV light through its shape and focal direction, in essence easily doubling the Ultraviolet germicidal properties.

While in the foregoing specification this invention has been described in relation to certain preferred embodiments thereof, and many details have been set forth for the purpose of illustration, it will be apparent to those skilled in the art that the invention is susceptible to additional embodiments and that certain details described herein can be varied considerably without departing from the basic principles of the invention.

The invention claimed is:

1. A metallic photocatalytic oxidation reflector comprising:
    two elongated U support structures having two first arm portions each having a first and second end, two second arm portions each having a first and second end, two U shaped connector bridges, an elongated substrate layer having a first surface and a second surface, a metal oxide coated substrate layer, and a base;
    wherein a first end of one of the first arm portions is connected to one end of one of the U shaped bridges and the first end of one of the second arm portions is connected to the other end of the same U shaped bridge;
    wherein the second U shaped bridge connects the first ends of the other first arm portions and second arm portions in a corresponding manner and the second ends of both the first arm portions and the second arm portions are connected to the base such that both elongated U structures are in a fixed position parallel to one another forming two elongated U structures facing one another in a mirror image position;
    wherein a support structure flange is disposed on each of the first arm portions and the second arm portions; extending outwardly towards an exterior of the support structures such that a first flat surface of the support structure flange extending from the first arm portion opposes and is parallel to a first flat surface extending outwardly from the second arm portion that is connected to the same U shaped bridge;
    wherein a second pair of support structure flanges are arranged correspondingly on the second pair of the first arm portions and the second arm portions the support structure flange extending from the second end of the first and second arm portions to near the first end of the first and second arm portions;
    wherein the elongated substrate layer is V shaped in cross section along its length having a substrate layer flange running along the length of the longitudinal edges of the substrate layer, the first surface forming an interior portion of the V shaped substrate layer and substrate layer flange and the second surface forming an exterior portion of the V shaped substrate layer and substrate layer flange;
    wherein the elongated substrate layer is dimensioned such that the first surface of the substrate layer flange aligns and attaches to the first side of the support structure flange disposed on the first and the second arm portions of the support structure;
    wherein a first substrate layer is attached to the structure flange joining the two first arm portions;
    wherein an apex of the V shaped first substrate layer faces the second arm portions and the first surface of the substrate layer flange and a second substrate layer is attached to the first side of the support structure flange disposed on the second arm portions such that the apex of the V shaped substrate layer of the second substrate layer faces the apex of the V shaped substrate layer the first substrate layer;
    the metal oxide coated substrate layer having the same general dimensions and shape as the elongated substrate layer having a first coated substrate surface, a second coated substrate surface, and a coated substrate layer flange, the first coated substrate surface forming an interior portion of a V shaped coated substrate layer and the second coated substrate surface forming an exterior portion of the V shaped coated substrate layer, and the coated substrate flange attaches to a longitudinal edge of the coated substrate layer;
    wherein the coated substrate layer is sized to fit on the second surface of the elongated substrate layer and the first surface of the coated substrate layer flange is in contact with the second surface of coated substrate layer flange; and
    a plurality of openings formed in at least a portion of the coated substrate layer.

2. The metallic photocatalytic oxidation reflector of claim 1 wherein the metal oxide coated substrate layer is comprised of titanium dioxide.

\* \* \* \* \*